United States Patent [19]
Viertl et al.

[11] Patent Number: 5,963,882
[45] Date of Patent: Oct. 5, 1999

[54] ULTRASONIC PULSER/RECEIVER FOR ULTRASONIC TEST EQUIPMENT

[75] Inventors: John R. M. Viertl, Niskayuna; Elizabeth L. Dixon, Delanson; Mederic E. Auger, Schenectady, all of N.Y.

[73] Assignee: General Electric Company, Schenectady, N.Y.

[21] Appl. No.: 08/727,691

[22] Filed: Oct. 8, 1996

[51] Int. Cl.$^6$ ................................................. G01N 29/00
[52] U.S. Cl. .......................... 702/39; 702/104; 73/609; 73/628
[58] Field of Search .................... 364/507, 550, 364/480, 492, 494, 146; 73/596, 602, 609, 618, 620, 634, 622, 628, 626, 610–612; 702/39, 104

[56] References Cited

U.S. PATENT DOCUMENTS

| | | | |
|---|---|---|---|
| 4,229,796 | 10/1980 | Garrett | 702/39 |
| 4,752,895 | 6/1988 | Sarr | 364/550 |
| 4,755,953 | 7/1988 | Geithman et al. | 364/507 |
| 4,799,167 | 1/1989 | Sarr | 364/507 |
| 4,799,168 | 1/1989 | Sarr | 364/507 |
| 5,386,360 | 1/1995 | Wilson et al. | 364/146 |
| 5,445,029 | 8/1995 | Falsetti et al. | 73/609 |
| 5,618,994 | 4/1997 | Falsetti et al. | 73/602 |

*Primary Examiner*—Marc S. Hoff
*Assistant Examiner*—Bryan Bui
*Attorney, Agent, or Firm*—Nixon & Vanderhye

[57] ABSTRACT

A configuration flexible computer-controlled ultrasonic diagnostic test equipment arrangement for examining large turbine rotors incorporates improved ultrasonic signal "pulser-receiver" circuitry that is used to drive one or more an ultrasonic transducers and to receive and amplify ultrasonic returns from a specimen under test. The improved pulser-receiver circuitry comprises both an ultrasonic pulse generating circuit and an associated ultrasonic return signal linear amplification circuit. The pulse generating circuitry and the ultrasonic return signal amplification circuitry are modular and functionally independent of each other and, consequently, may be used together in the testing system or as stand-alone instrumentation. Overall ultrasonic diagnostic system flexibility is significantly enhanced by providing improved pulser-receiver circuitry with digitally driveable computer control inputs in addition to manual controls to enable selecting initial parameters and transducer position settings. A menu-driven display machine-operator interface is also provided as a user-friendly and efficient means for setting and accessing system configuration information and test data.

20 Claims, 7 Drawing Sheets

ULTRASONIC PULSER/RECEIVER FOR ULTRASONIC TEST EQUIPMENT

CROSS-REFERENCE TO RELATED PATENTS AND APPLICATIONS

This application is related to the following commonly assigned patent and application, which are hereby incorporated by reference:

U.S. Pat. No. 5,445,029, filed Nov. 8, 1993, entitled "Calibration And Flaw Detection Method For Ultrasonic Inspection Of Acoustically Noisy Materials" and application, Ser. No. 08/421,929, filed Apr. 14, 1995, entitled "Calibration Method Using a Pitch-catch Arrangement for Ultrasonic Inspection of Acoustically Noisy Materials", now U.S. Pat. No. 5,618,994.

TECHNICAL FIELD

The present invention generally relates to ultrasonic equipment for performing computerized ultrasonic testing and, in particular, to a method and apparatus for ultrasonic inspection of solid rotor forgings used in the construction of large turbine and generator rotors. More specifically, the invention relates to a modular and user-configurable pulser-receiver front end for use with computer controlled ultrasonic diagnostics test equipment.

BACKGROUND AND SUMMARY OF THE INVENTION

In many environments, the structural integrity of certain critical components of a particular system or apparatus is of the utmost importance in ensuring against future failures. For example, components used in the construction of large turbines are typically subjected to great mechanical stresses and must be able to withstand exposure to extreme temperatures as well as high velocity corrosive gas streams. Accordingly, to provide high performance characteristics and improve the reliability of a turbine, strict requirements are imposed on the structural integrity of its constituent parts. In this regard, the use of various ultrasonic examination techniques has proven to be advantageous in providing useful information concerning the internal structural integrity of part forgings. In particular, two ultrasonic inspection techniques used for the nondestructive testing of turbine rotor forgings include a "Pitch-Catch" technique that employs a pair of ultrasonic transducers and a "Pulse-Echo" technique that uses only a single transducer. Conventional manual testing techniques relied upon an operator to observe a CRT and manually record all occurrences of an ultrasonic echo exceeding a predetermined threshold. The present invention concerns improvements to ultrasonic testing arrangements of the above sort that utilize automated computer controlled data acquisition techniques. A primary motivation to automate ultrasonic rotor testing was to improve the detection of "indication structures" (i.e., potential structural flaws or voids) and reduce operator induced variability of test data results. Although an automated system substantially removes operator variability, it requires a certain degree of signal processing and analysis to distinguish between real signals and noise. Computer-controlled automated testing arrangements are ideally suited to provide the needed signal processing and analysis. Accordingly, the present invention as described below provides improved automated data acquisition techniques and control electronics for use in computer-controlled ultrasonic testing systems.

In FIG. 1, the basic mechanical arrangement, 100, of an ultrasonic diagnostic system used for examining a turbine rotor is illustrated. In addition, a block diagram of the data acquisition and control system electronics, 130, in accordance the present invention is also shown. Although the system depicted in FIG. 1 illustrates a "pulse-echo" testing arrangement that requires only a single transducer, the improved data acquisition and control system as contemplated by the present invention is also applicable to testing arrangements utilizing multiple transducers, for example, a "pitch-catch" or other diagnostic technique.

During ultrasonic testing, a turbine rotor forging 110 is rotated by electric motor driven mechanical rollers ("power rollers") 120 and 121. An ultrasonic transducer 125, located at the end of a support arm, is capable of controlled movement relative to the rotor axial direction. The speed of the rotor rotation, starting position and motion of the transducer, as well as the ultrasonic return soundings data received by the transducer are respectively controlled and processed by data acquisition and control system 130. In the improved data acquisition and control system arrangement contemplated in accordance with the present invention, the motion control circuitry 149 and motion control signal amplifier circuitry 150 for the transducer positional servo (or stepper motors) and the power driving roller 120–121 are preferably located on one or more modular plug-in circuit boards ("circuit cards") associated with a system diagnostic and control computer, 131. While the rotor is being rotated, pulser-receiver unit 140 stimulates one or more transducer 125 to generate ultrasonic pulses and also monitors the same to receive ultrasonic soundings for storage and analysis. Diagnostic data is acquired in the form of ultrasonic soundings produced and received through transducer 125 via ultrasonic pulser-receiver unit 140. Signals from transducer 125 are converted from analog to digital form by A/D (analog-to-digital) signal converter 141 and stored in a memory 142 associated with the A/D circuitry. The stored digital signals are then transmitted on request to diagnostic and control computer 131 for processing. System computer 131 also may then compress these digital signals and store them as data records in a more permanent storage medium 132.

In accordance with the present invention, the flexibility of the diagnostic system is enhanced by the provision of a modular computer-controllable pulser-receiver that is capable of providing ultrasonic pulse generating functions and signal amplifying functions either separately—as would be available, for example, through independent circuit modules—or in concert as a single instrument under computer control. Accordingly, pulser-receiver unit 140 of the present invention preferably consists of one or more modules or circuit cards that plug (connect) into a "mother" board (i.e., a circuit board that has suitable electrical buses for providing power, ground, signal data and the like between several cards or modules) for easy access, removal and/or replacement. The pulser-receiver unit mother board (not shown) and its associated plug-in circuit cards are preferably contained within a suitable electrically shielded housing (not shown) to minimize the radiating of electrical noise. In the example arrangement of the present invention shown in the accompanying figures, an ultrasonic pulse generator and pulse duration controller circuit ("pulser control") and a transducer position control logic circuit ("relay control logic") are combined together as an integral module on a single circuit card, although other divisions of function and/or modular arrangements are also possible. In accordance with one aspect of the present invention, the "pulser control" generates ultrasonic pulses of specific durations and also allows either manual or computerized control over the direction (angle) of the ultrasonic beam. A separate circuit card module contains an analog logrithmic amplifier circuit that provides selectable logrithmic amounts of signal gain for both video and RF compatible outputs. Preferably, the mother board is outfitted with a plurality of signal/power bus interface connectors for easy addition of other custom function modules as desired—such as another ultrasonic signal amplifier card, a CRT display driver card, or the like.

In accordance with another aspect of the present invention, A/D converter 141 and associated memory 142 of the present invention are preferably provided on "plug-in" type circuit boards associated with system computer 131. In accordance with still a further aspect of the present invention, a data acquisition and control system arrangement is presented that can easily accommodate multiple pulser-receiver modules to provide individual or cooperative use of several ultrasonic transducers such as used, for example, in a "pitch-catch" diagnostic technique.

Previous to the present invention, pulser-receiver functions were obtained by using a General Electric (GE) AMPUT™ Pulser/Receiver unit or a printed circuit board version of this unit. Although the GE AMPUT™ Pulser/Receiver performs satisfactorily in manually controlled ultrasonic testing arrangements, its fixed hardware design does not quite provide a degree of flexibility which would permit a more comprehensive utilization of the many capabilities that a computer controlled data acquisition arrangement can offer. For example, although the GE AMPUT™ Pulser/Receiver is triggerable from an external source (e.g., a remote computer), its constituent circuit functions and settings are not directly computer controllable. It is not possible to select and vary operating parameters such as gain, sensitivity, frequency range, etc., either remotely or under programmed control. Moreover, it is not possible to easily modify the ultrasonic signal amplifier response characteristics or utilize the signal amplifier and pulser functions individually or independently of one another may be required, for example, in non-ultrasonic applications.

Often, during an ultrasonic examination of turbine parts, it is desirable to be able to rearrange the relative positions of ultrasonic transducers including the transducer housing/coupling support mechanisms and/or the overall physical configuration of the test equipment to accommodate new or different components, testing procedures and/or applications. When using the conventional GE AMPUT™ Pulser/Receiver unit, such flexibility is not readily achievable. Therefore, in accordance with the present invention, an improved pluser-receiver is provided that can be operated as separate modules performing respective "pulser" and "receiver" functions or as a single integrated pulser-receiver unit. Moreover, the pluser-receiver electronics of the present invention may be operated independently of the rest of the ultrasonic test equipment as a stand alone instrument. The modular "plug-in" architecture of the improved pulser-receiver of the present invention also allows test configurations that need to use multiple pulser-receiver circuit pairs for operations with multiple transducers.

Accordingly, the described embodiment of the present invention provides an improved pulser-receiver that results in a configuration variable ultrasonic testing system and provides an improved operator interface method for the computerized operation and control of ultrasonic testing equipment. In addition, the present invention provides a menu-driven interactive operator-machine interface means for the system control computer that is compatible with the improved pulser-receiver for configuring the ultrasonic test equipment and controlling pulser-receiver functions.

BRIEF DESCRIPTION OF THE DRAWINGS

These and other features and advantages of the present invention will become more completely understood by referring to the following detailed description of presently preferred exemplary embodiments in conjunction with the FIGURES in which like reference numerals refer to like elements throughout.

DETAILED DESCRIPTION OF THE PRESENTLY PREFERRED EMBODIMENT

In the following description, for purposes of explanation and not limitation, specific details are set forth, such as particular circuits, circuit components, interfaces, techniques, etc. in order to provide a thorough understanding of the present invention. However, it will be apparent to one skilled in the art that the present invention may be practiced in other embodiments that depart from these specific details. In other instances, detailed descriptions of well known methods and programming procedures, devices, and circuits are omitted so not to obscure the description of the present invention with unnecessary detail.

Figure 1A:
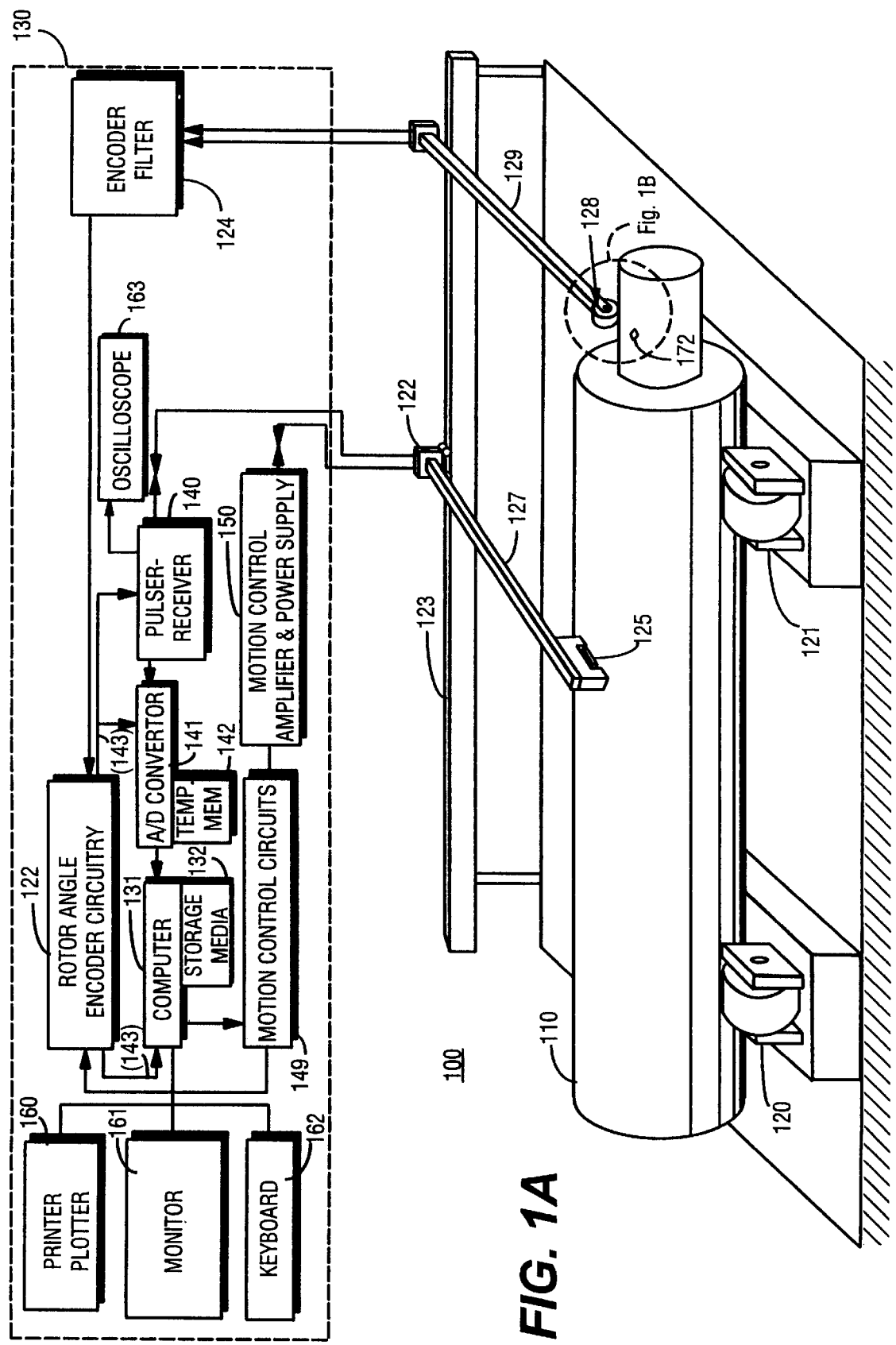
FIG. 1A is a schematic block diagram of a computer-controlled ultrasonic examination system for nondestructive testing of large turbine rotors in accordance with an example embodiment of the present invention.

As discussed above, FIG. 1A illustrates the basic mechanical configuration of an ultrasonic inspection system, 100, used for examining and testing large turbine rotor forgings (e.g., on the order of 10–250 tons). Turbine rotor forging 110 is supported and rotated by electric motor driven "power rollers" 120 and 121. Ultrasonic transducer 125, located at the end of support arm 127, is capable of controlled movement relative in the axial direction of rotor 110. The speed of the rotor rotation, starting position and motion of the transducer, as well as the ultrasonic return soundings data received by the transducer are respectively controlled and processed by data acquisition and control system 130. Transducer support arm 127 is attached to mechanical drive 122 for moving the support arm and transducer 125 parallel to the axis of rotor 110. Preferably, transducer 125 rests on the rotor body surface. Drive mechanism 122 is supported on rack 123 and a mechanical driving arrangement, such as a rack and pinion mechanism driven by a single axis servo, is utilized in conjunction with support rack 123 to provide the axial movement of the transducer with respect to rotor 110. Servo motion control relays 149 and amplifier circuitry 150 are provided to interface computer generated control signals to the transducer and power roller drive mechanisms.

During an ultrasonic diagnostic test, rotor 110 is rotated while transducer 125 is held stationary, tracing a circumferential scan path over the rotor surface. After a full revolution of data is obtained, transducer arm 127 is stepped axially along rotor 110 to a new position for the next circumferential scan. The axial step size is preferably a distance that is approximately one-eighth of the transverse (i.e., axial) ultrasonic beam spread, as measured at the center of the rotor. While the axial step is occurring, the obtained data is compressed, stored and displayed on system monitor 161. This operation is continued until a preselected axial length of the rotor has been covered. Thus, transducer 125 essentially follows a circumferential-axial path over the surface of the rotor and each revolution of the rotor provides a single cross-sectional "data slice" of ultrasonic information about the rotor.

In one preferred embodiment of the present invention, transducer 125 is a an oiled coupled PZT transducer excited at 2.25 MHz by pulser-receiver circuitry 140. During testing, A/D circuitry 141 is initialized and left in an armed state. It is triggered by a "pulse-on-position" signal (143) from rotor angle encoder circuit 122. This same signal also triggers pulser-receiver 140 and generates an interrupt within computer 131. The triggered ultrasonic pulser-receiver circuit sends an excitation pulse to transducer 125 which emits an ultrasonic pulse. The ultrasonic pulse generated at transducer 125 enters rotor 110, propagates along the rotor diameter, reflects from various defects or "targets" within the rotor, and is detected by the same transducer (e.g., for pulse-echo testing).

Transducer 125 receives the reflected ultrasonic pulses (ultrasonic soundings or "indications") and sends them back to pulser-receiver 140 for amplification. The detected return signal is amplified within pulser-receiver circuitry 140 by a logarithmic amplifier (discussed below) that has a 78 dB (approximately) dynamic range. The logarithmic amplifier is preferably adjusted so that a 20 dB signal change produces a one volt change in output. The output of the logarithmic amplifier is full wave rectified and provided to A/D convertor 141 which preferably has at least a 4.0 volt range and provides 64 digital output levels for each volt.

Each received ultrasonic return signal amplitude record is digitized by A/D convertor 141 into 8 bits using a 25 MHz sampling rate. Sampling an ultrasonic return at 25 MHz corresponds to a one-way metal path of 0.12 mm. The range of an ultrasonic test pulse is preferably set to have a length of approximately three to five oscillations at 2.25 MHz. This corresponds to a range extent of approximately 0.0079 to 0.0132 meters. Accordingly, each oscillation of the ultrasonic signal pulse can be represented by approximately 11 data points and each complete ultrasonic pulse by 33 to 55 data points. The digitized ultrasonic return is divided into 512 range bins which span the time from ultrasonic pulse generation to approximately one microsecond beyond the duration required to receive the reflected "back wall" echo signal. This insures that the system will always capture the "back wall" echo signal and thus provide an ultrasonic signal amplitude for that record that is adequate for evaluation.

To reduce data storage requirements, the acquired data is compressed by selecting and retaining the maximum amplitude in each range bin. Ultrasonic "indication" sets are then built from the compressed records by searching each range bin for a maximum signal value. Each bin which originally contained 11 data points is replaced by the maximum value in the bin. This approach guarantees that no indication signal will be missed while still providing a data compression ratio of about eleven to one. Preferably, ultrasonic amplitude data is recorded as the logarithm of the original signal. In addition to amplitude data, both axial and angular position data are also recorded in the compressed data records.

Figure 1B:
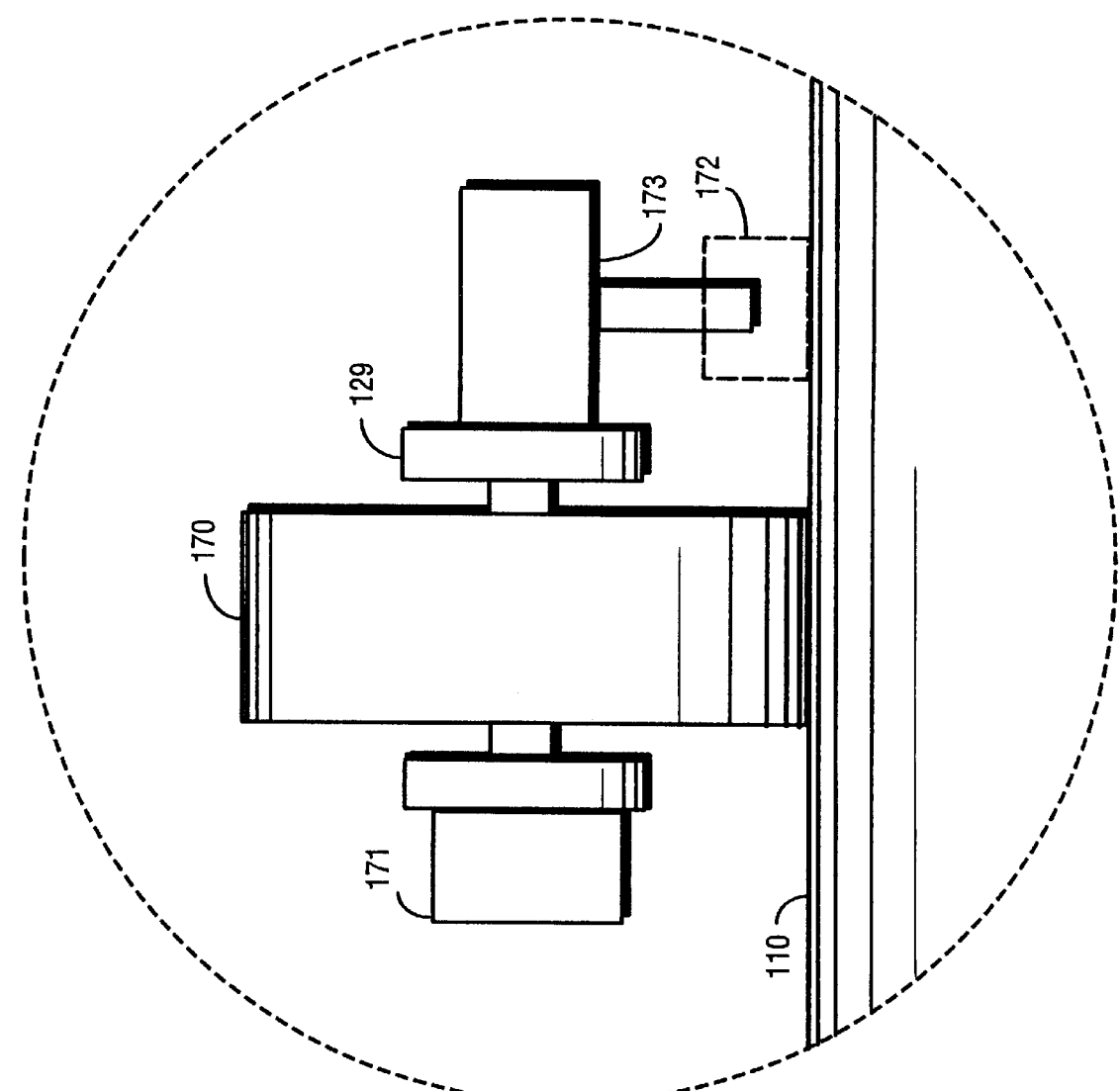
FIG. 1B is a detailed diagram of the rotor angle encoder mechanism of FIG. 1A.

An angular reference both for a "zero degree" reference position for each circumferential scan and for incremental one-half degree circumferential steps during each circumferential scan is based upon signal pulses obtained from a rotor angle encoder arrangement shown in greater detail in FIG. 1B. Friction wheel 170, rides the surface of turbine rotor 110 at the end of support arm 129. Rotation of friction wheel 170 is detected and monitored by a conventional rotation indicator, 171, such as an axial driven electro-optical pulse generator. Mechanical "trip" device 172 is magnetically attached to a peripheral location on the rotor surface and the passage of the trip device is detected by micro-switch 173 once per each full rotation of the rotor. The "zero degree" reference point for ultrasonic scanning is set up on rotor 110 by magnetically attaching a mechanical "trip" device to a peripheral location on the rotor. The angular position of the rotor is provided by monitoring the rotation of a contacting idler roller or "friction wheel" 128. The angular position of friction wheel 128 may be obtained by a conventional angular position indicator (e.g., an optical encoder) mounted on friction wheel support arm 129. Once per each revolution of the rotor, the passage of the trip device is detected by a micro-switch also attached to friction wheel support arm 129.

Since this "once-per-rev" switch may sometimes be located a considerable distance from the rest of the diagnostic and control electronics of the system, an unacceptable amount of interfering electrical noise may be picked up on the connecting cable. This can also occur with signals acquired from a rotor angle encoder located at the rotor. Moreover, a mechanical micro-switch naturally "bounces" whenever it is actuated, creating additional electrical noise. Consequently, and in accordance with a preferred embodiment of the present invention, the "once-per-rev" signal obtained from the micro-switch is de-bounced, filtered by low pass filter circuit 124 and used to trigger a re-setable "one-shot" (i.e., a monostable multivibrator circuit) to reconstitute the signal into a clean trigger pulse for delivery to rotor angle signal encoder circuitry 122.

Encoder circuitry 122 interprets the signals from rotor angle indicator 171 and from micro-switch 173 to provide information on the angular position of the rotor and to determine the end of each complete revolution of the rotor. The angular position indications and the "end of rev" indication provide two types of interrupt signals to system computer 131: 1) a trigger signal for the A/D (analog-to-digital) convertor circuitry used to convert the analog transducer signals to digital, and 2) a trigger signal for the ultrasonic pulser-receiver circuitry. Together these two interrupt signals are used to synchronize the generation of ultrasonic diagnostic pulses and permit a "pulse on position" operation of the system wherein an ultrasonic diagnostic pulse can be generated at predetermined angular positions of the rotor.

In accordance with a further aspect of the present invention, an interrupt routine is provided within computer 131 that re-enables internal interrupt signal paths, queries the A/D circuitry, waits for a signal from the A/D circuitry indicating that signal digitization is completed, and then transfers the digitized ultrasonic signal from temporary memory 142 to the computer memory or to mass storage medium 132 (e.g., a read/write optical disk memory device). Computer 131 then sends the A/D circuitry a request to "re-arm" for the acquisition of the next ultrasonic soundings signal from the pulser-receiver. Once per each revolution of the rotor, the interrupt marking the "end of rev" replaces a "normal" encoder angle interrupt (i.e., the interrupts generated by the mechanical rotor angle encoder during power roller rotation) and a certain amount of "end of revolution" data processing is carried out by computer 131. This feature of the present invention allows data collection to begin at any desired annular position of the rotor and continue until all planned records have been captured.

Data Analysis and Ultrasonic Indication Set Building

The ultrasonic indication set building process begins with the selection of ultrasonic data that exceeds a range dependent threshold. The operator enters the threshold data and selects the number of adjacent range bins with an amplitude greater than the threshold. These parameters for the threshold and the ultrasonic echo are used in the data analysis. The latter parameter insures that the recorded signal is an authentic echo and not a noise spike. After this, actual set building can begin.

There are basically three stages to the indication set building process, one for each independent coordinate. At each of these stages the ultrasonic data determines the extremes of the coordinates. Additional operations are performed on the data such as testing for and saving the peak ultrasonic amplitude, and its associated coordinate values. Since indication sets are formed from targets that move through the ultrasonic beam both on the near and far side of the rotor centerline as the rotor is rotated during testing, duplicate indication sets may be formed. These duplicates are combined by comparing the completed indication sets with those that are separated from each other by 180°. Its coordinate extremes are adjusted to reflect this combining of sets. The peak amplitude and coordinate values are compared and then used to determine the "effective flat bottom hole diameter."

Pulser-Receiver Operation

Figure 2:
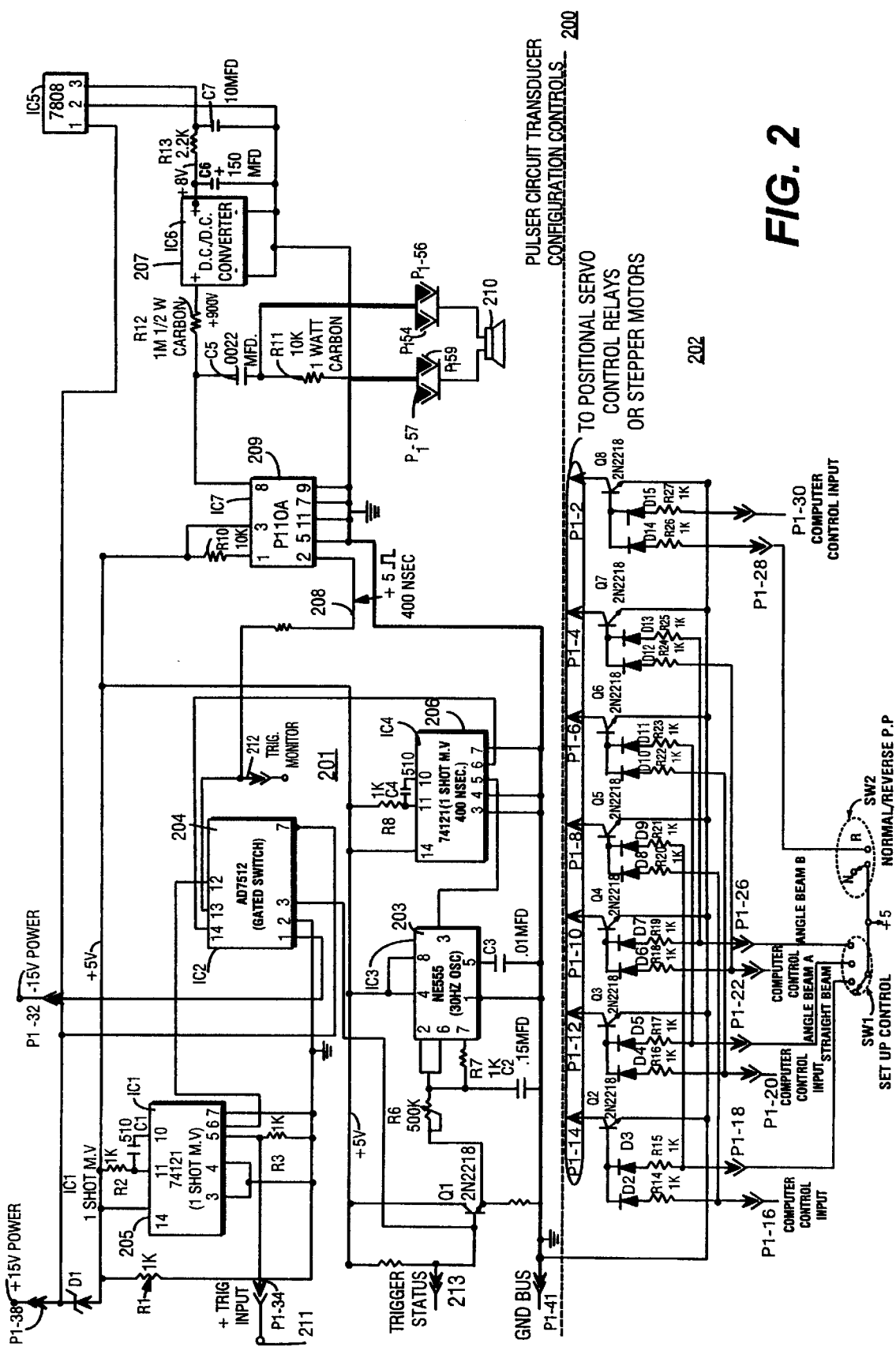
FIG. 2 is a detailed schematic of an ultrasonic transducer pulser controller circuit and transducer position control logic circuit for an example embodiment of the pulser-receiver unit in accordance with the present invention.

Referring now to FIG. 2, a schematic diagram of an ultrasonic transducer "pulser" controller and transducer positional servo relay control logic module for an example embodiment of a pulser-receiver unit in accordance with the present invention is discussed. Basically, an electronic "pulser" unit generates one or more pulse trains of controlled frequency and duration which are used to excite an ultrasonic transducer to emit ultrasonic sound waves of a desired duration and character. In accordance with the present invention, a modularly configured pulser-receiver unit comprises both an ultrasonic pulse generating circuit and an associated ultrasonic return signal linear amplification circuit arranged on a plurality of circuit cards (or modules) which are detachably connected to a common "mother" board or module which provides power, ground and signal for all modules. Thus, for example, the pulse generating circuitry and the ultrasonic return signal amplification circuitry can be configured functionally independent of each other and may be used separately as stand-alone instrumentation.

As illustrated in FIG. 2, a Pulser Controller And Transducer Positioning Servo Relay Control Logic Module, 200, consists of a transducer excitation pulse train generating and control section, 201, for driving one or more ultrasonic transducers, and a transducer position servo relay control section, 202, to generate servo relay control signals for varying the orientation and position of the transducer (or transducers) and hence, the angle and position of a resultant ultrasonic beam. P1–2 through P1–59 designate power and signal input/output terminals provided on module 200 for interconnection to a mother board or other circuit modules. Transducer excitation control section 201 utilizes an NE555 timer/oscillator 203 and one-shot 206 to generate pulses at a desired frequency (e.g., 30 Hz) and a predetermined pulse width (e.g., 400 nsec). One-shot 205 and gated switch 204 control the initiation and duration of the transducer excitation pulse train. A high voltage output by D.C./D.C. voltage converter 207 is modulated by pulses 208 from gated switch 204 and capacitively coupled via amplifier 209 to one or more ultrasonic transducers 210. An external "trigger" signal must be provided at input terminal 211 to one-shot 205 for initiating the generating of the high voltage transducer excitation pulse train ultimately produced at terminals P1–57/59 and P1–54/56. The external trigger signal is provided by the system processor 130 or can be obtained from any other suitable desired external source. In addition, a trigger signal monitor output 212 is made available at gated switch 204 and provided, in this example, to the system digital processor 130 for monitoring the trigger output from gated switch 204. A trigger pulse status signal is also made available for monitoring at terminal 213.

Transducer position servo relay control section 202 consists of multiple current-sinking transistors Q2–Q8, diodes D2–D15, resistors R14–R27 and selector switches SW1 and SW2 in an arrangement that allows either a manual or a computer driven selection of ultrasonic beam character (for example: "straight beam", "angle beam A", "angle beam B"). Outputs terminals P1–2 through P1–14 at the collectors of transistors Q2–Q8 provide signals to control servo relays (not shown) for positioning the ultrasonic transducers. Switch SW1 allows manual selection of ultrasonic beam and angle while SW2 allows selection of either "normal" or "reverse" scan modes. The "C.C." position of SW1 allows a computer controlled selection of beam and character via inputs P1–16, P1–20, P1–24 and P1–28.

A list of integrated circuit functions corresponding to components in the pulser control and relay control logic module as depicted by FIG. 2 is presented immediately below.

IC1—74121 (one-shot/monostable multivibrator)
IC2—AD7512 (gated switch)
IC3—NE555 (30 Hz oscilator)
IC4—74121 (one-shot/monostable multivibrator)
IC5—7808 (conventional IC)
IC6—D.C./D.C. converter
IC7—P110A amplifier Other components shown in FIG. 2 are well known conventional electronic circuit components, rated as indicated.

Figure 3A:
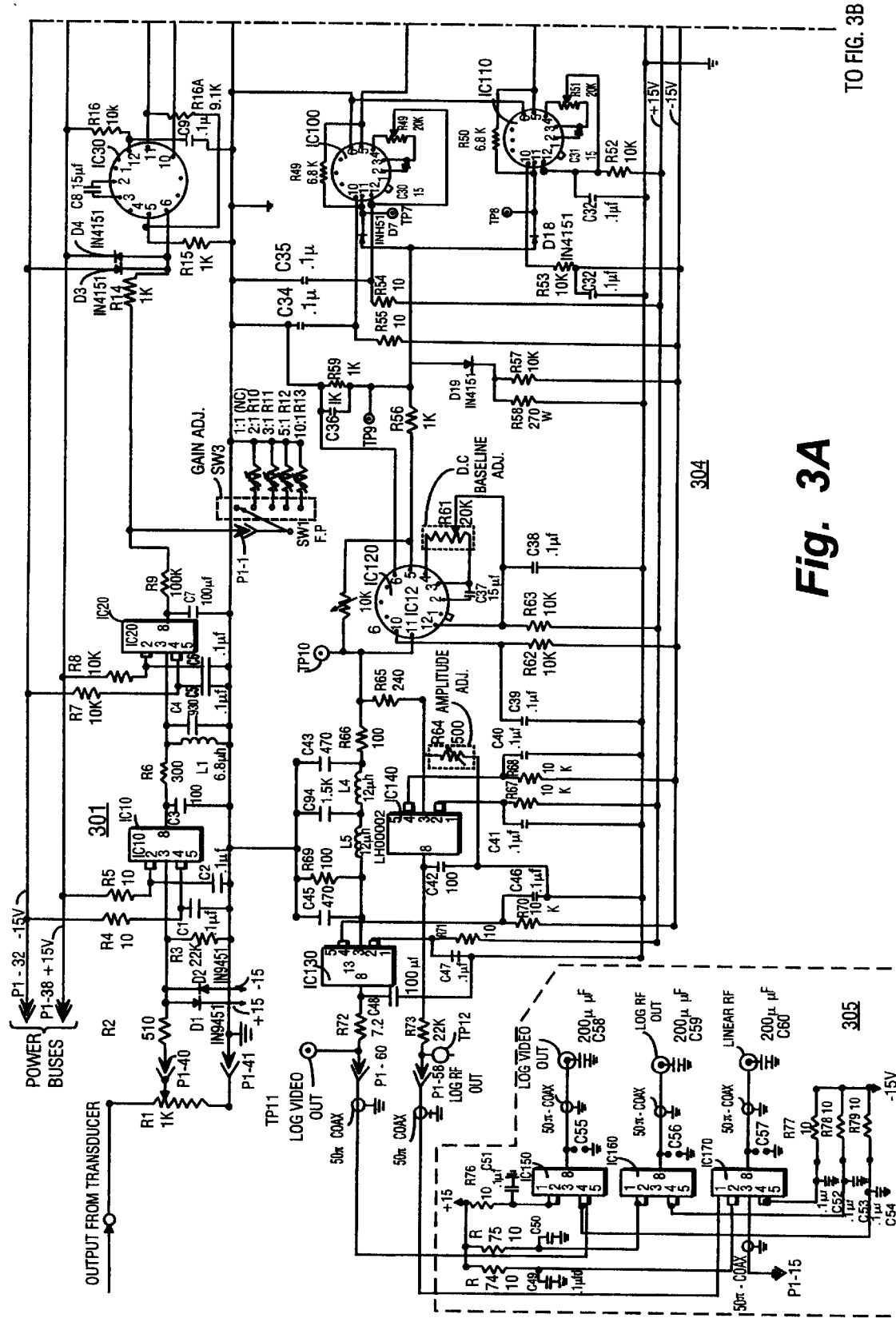
FIGS. 3A and 3B are a detailed schematic of an analog logrithmic amplifier circuit of the pulser-receiver in accordance with the present invention.
Figure 3B:
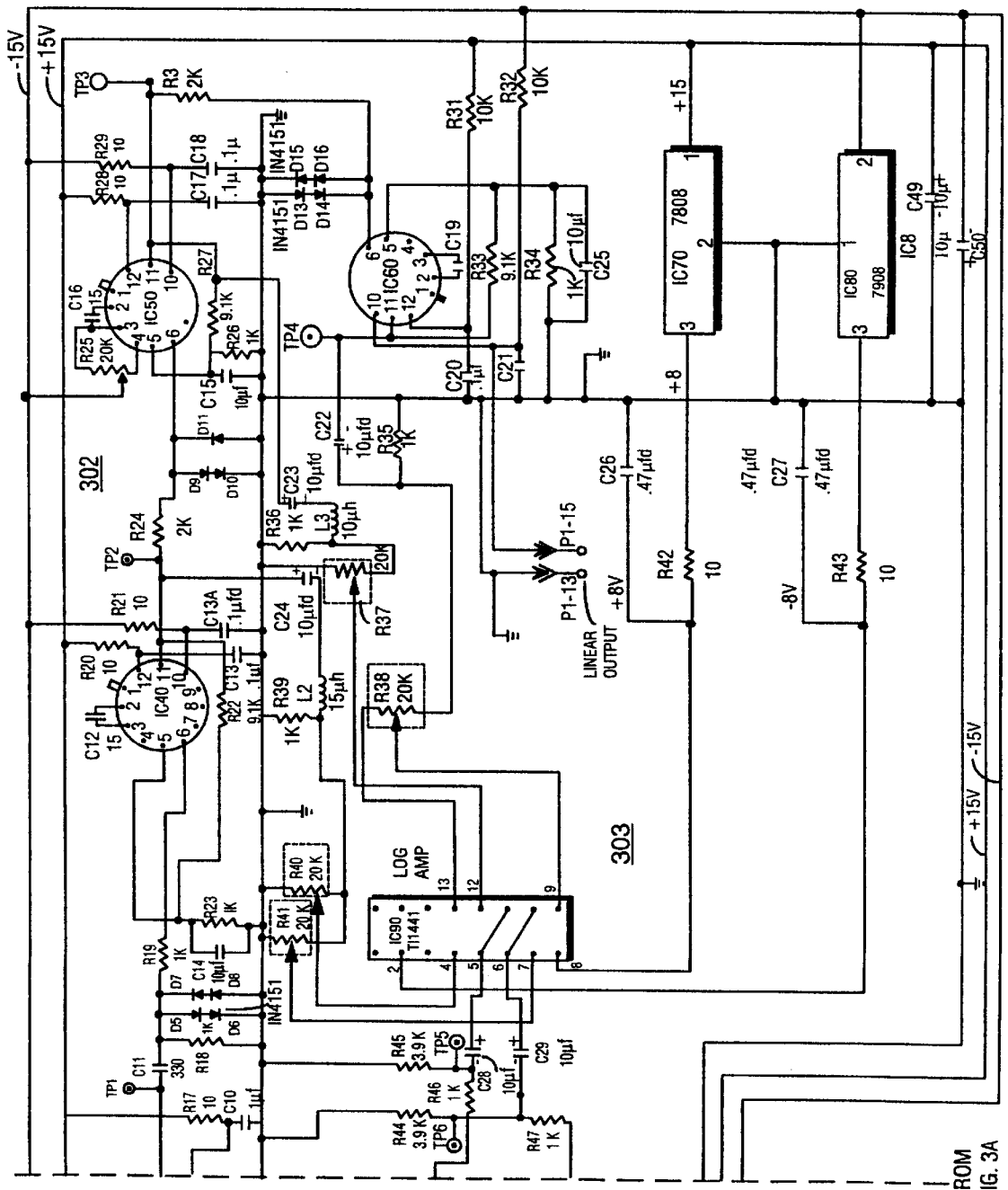

Referring now to FIGS. 3A and 3B, the schematic of the analog logrithmic amplifier circuit module is discussed. In accordance with the present invention, the analog logrithmic amplifier circuit module is preferably provided as a separate piece of hardware from the pulser module described above. Basically, the analog logrithmic amplifier circuit module consists of a low-noise adjustable-gain signal amplification section and an optional output buffering section. TP1 through TP11 indicate convenient test points within the logrithmic amplifier circuitry for facilitating ordinary maintenance and repair. Signal amplification section 301 consists of a series configuration of active operational amplifiers, IC10 through IC60, with associated R-L-C filter and feedback circuitry followed by an integrated circuit logrithmic amplifier, IC9, having presetable logrithmic gain characteristics. A signal, for example an output signal from a receiving ultrasonic transducer, is provided to the logrithmic amplifier module at input terminals P1–40 and P1–41. An optional input attenuator, R1 (which may be incorporated into the amplifier module or provided apart from it as desired), allows adjustment of input signal levels to prevent over-driving the active input stage filter components comprising operational amplifiers IC10 and IC20. A multi-position switch, SW3, connected to a plurality of adjustable resistors, R10–R13, follows op-amp IC20 at the input of IC30 and acts as an adjustable voltage divider network. This arrangement provides a selection of various different gain ratios (e.g., 1:1, 2:1, 5:1, etc.) to be obtained form linear amplification stage, 302, which basically consists of amplifiers IC30, IC40, IC50 and IC60. The amplified "linear" output of amplification stage 302 is optionally made available at the terminals designated as P1–13 and P1–15 (FIG. 3B).

The linearly amplified transducer signal at the output of IC60 is next provided to logrithmic amplification stage 303. Basically, the logrithmic amplification stage consists of an integrated logrithmic amplifier, IC90, which is provided with an adjustable input signal attenuator, R37, and additional potentiometers R37, R38, R40 and R41 for presetting logrithmic gain characteristics. Bipolar outputs of logrithmic amplifier IC90 are mixed and buffered by integrated linear amplifiers IC100 and IC110 in output section 304. The outputs from IC100 and IC110 are provided to linear amplifier IC120. A potentiometer, R61, associated with IC120 provides a means for setting/adjusting a D.C. baseline for the logrithmically amplified output. The output from IC 120 is coupled through an RLC filter to op-amp output buffer IC130 to provide a logrithmic video output signal and is also coupled to op-amp output buffer IC140 and associated RC filter/feedback circuitry to provide a logrithmic RF output. Potentiometer R64 associated with IC140 allows fine adjustment of RF output amplitude.

Logrithmic video and logrithmic RF signal output is provided at terminals P1–60 and P1–58, respectively. These signal may be used to provide an oscilloscope type display of the received ultrasonic waveforms. An optional output buffering section 305 may also be provided for the logrithmic video, logrithmic RF and linear RF signal outputs making each suitable for driving a conventional 50-ohm coaxial cable load.

A list of integrated circuit devices corresponding to the designations used in FIGS. 3A and 3B is presented below. Other components shown in the figures are conventional electronic components, rated as indicated.

Figure 4A:
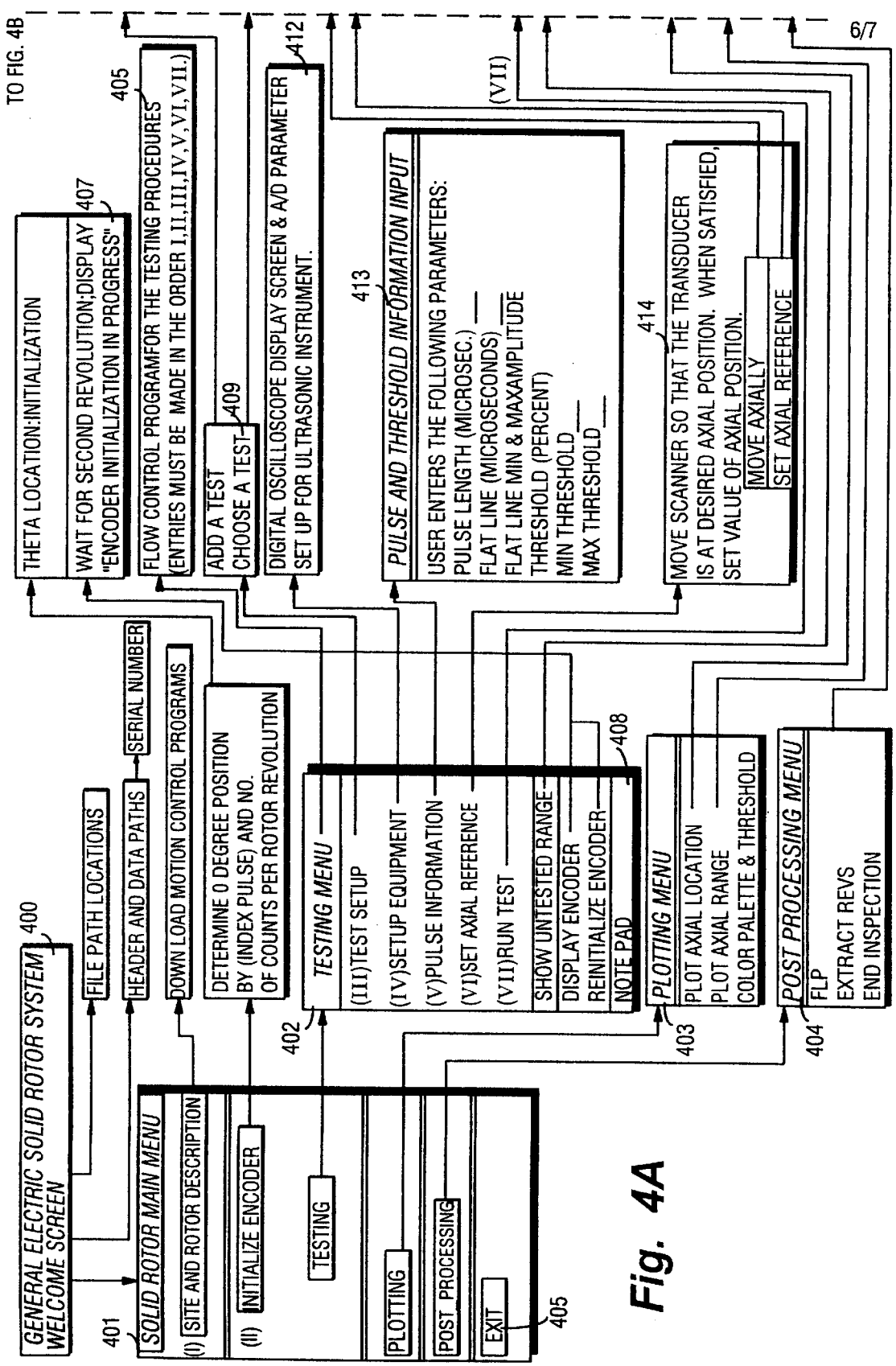
FIGS. 4A and 4B are software process specification diagrams illustrating primary functional and operational control processes of an example control program for a computer controlled system for performing ultrasonic examination of turbine rotors in accordance with the present invention.
Figure 4B:
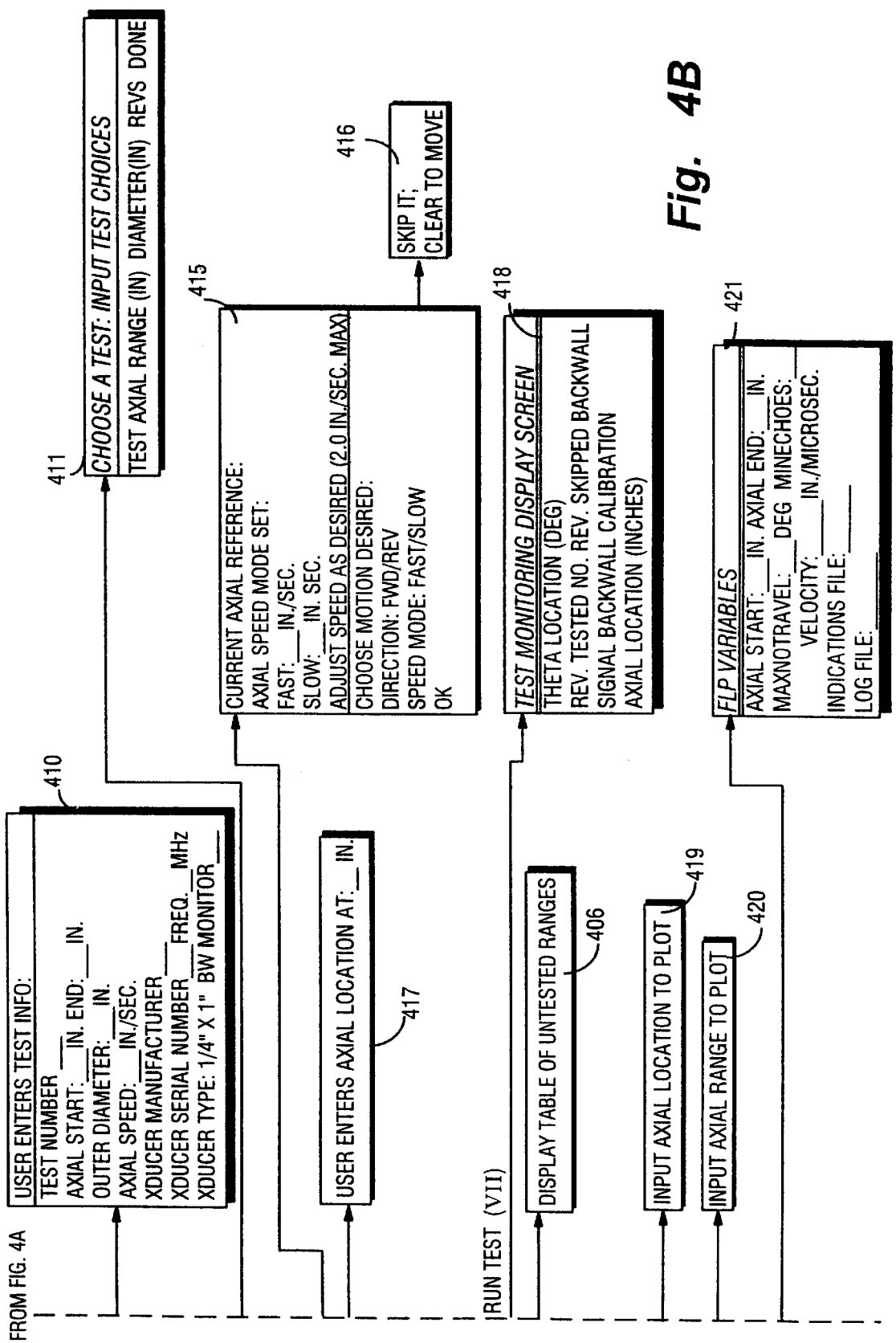

IC1—LH0002 Op Amp
IC2—LH0002 Op Amp
IC3—LH0032G Op Amp
IC4—LH0032G Op Amp
IC5—LH0032G Op Amp
IC6—LH0032G Op Amp
IC7—7808 (conventional IC)
IC8—7809 (conventional IC)
IC9—Logrithimic Amplifier
IC10—LH0032G Op Amp
IC11—LH0032G Op Amp
IC12—LH0032G Op Amp
IC13—LH0002 Op Amp
C14—LH0002 Op Amp
C15—LH0002 Op Amp
C16—LH0002 Op Amp
IC17—LH0002 Op Amp Referring now to FIGS. 4A and 4B, a software process pecification for an example control program for an embodiment of the present invention is explained. A preferred embodiment of the control program in accordance with the present invention utilizes interactive graphics or, for example, a Windows™ (trademark of Microsoft corp.) type man-machine display interface, the programming details of which can be readily implemented by a computer systems programmer of ordinary skill familiar with interactive interface programming in view of the process specification diagrams of FIGS. 4A and 4B.

Following the display of an initial system "welcome" screen 400, a main menu screen 401 is produced that allows a human operator to select between system functions and sub-menus for: 1) site and rotor descriptions (I),—e.g., to download (retrieve) desired scanning motion control programs from storage; 2) scanning-head position encoder initialization procedures (II)—which set the 0° reference position for the ultrasonic scanning head on the rotor; 3) testing procedure menu 402; 4) data plotting menu 403; 5) post processing menu 404; or 6) end of testing (i.e., program exit) option 405.

Selecting the testing menu 402 allows the entry of various parameter values used for conducting and controlling the ultrasonic scan tests. A test flow control program 405 utilizes operator-inputted parameter values to control the testing procedures for a particular ultrasonic test. Testing Menu 402 also provides access to a procedure for displaying a table of untested (non-tested) ranges 406, a procedure for displaying the scanning-head position encoder and/or reinitializing the position encoder 407, and a note pad 408 for making and storing various notations as needed or desired. Entry of ultrasonic test procedure parameters and the "setting up" of test equipment is conducted in a controlled logical fashion beginning with the entry of Test Setup and log information (III), continuing with Equipment initializing (IV) and Pulse and Threshold information input (V), Setting an Axial Reference position (VI), and finally, Running the Test (VII).

During an entry of Test Setup log information (III), an option to add (define) a "new" test setup or proceed with "old" (previously entered) test parameters is provided (as indicated at block 409). For each particular test setup configuration, test identification and parameter information such as a test number, axial starting and ending positions, axial scanning speed, and transducer manufacturer is entered by the operator (block 410). Alternatively, an old test setup configuration can be accessed (e.g., by test number) and/or altered (block 411).

Next, as indicated in block 412, the test equipment is initialized (e.g., parameters for the A/D converter are initialized for the particular ultrasonic test and a "digital oscilloscope" display screen is set up on the computer monitor). At this point, the rotor angle encoder signals are used to synchronize the ultrasonic pulser and the analog-to-digital conversion of the analog output from the logrithmic amplifier circuit. This is followed by a Pulse and Threshold information input step (V), wherein the operator is prompted to enter various parameters specifying the desired ultrasonic pulse characteristics and detection threshold values, as illustrated for example, in block 413.

Next, the scanning head positioning equipment 127 and 128 (FIG. 1) is activated and controlled to position the transducer(s) to a desired axial position, as indicated in block 414. The operator is presented with an option (414A) of setting a desired axial reference position directly by entering an axial position value (block 417) or coordinating a movement of the transducer head unit(s) by inputting movement parameters to interactive display areas, as indicated at blocks 415 and 416. Finally, a Run Test option (VII) may be selected by the operator and a Test Monitoring Display Screen menu procedure executes the desired ultrasonic tests and displays test conditions and results, as indicated at block 418.

Selecting Plotting Menu option 403 from Solid Rotor Testing System Main Menu 401, initiates a procedure which generates a graphic plot on the PC monitor screen (or via a printer/plotter) of the ultrasonic test results for a desired axial location and/or range after prompting for the desired axial location and range, as indicated at blocks 419 and 420. Selecting Post Processing Menu option 404 from Solid Rotor System Testing System Main Menu 401, initiates procedures which allow inputting parameters for interactively extracting, processing and categorizing test results data, for example, as indicated by FLP Variables menu procedures 421.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A computer controlled nondestructive testing system for performing ultrasonic inspections, comprising:
    a programmable digital processor; said processor generating trigger signals initiating transducer excitation, storing system configuration information and test data, and supporting a menu-driven user interactive system control interface;
    an ultrasonic transducer pulser-receiver unit electrically interfaced to said processor, said pulser-receiver unit comprising:
        ultrasonic transducer pulser circuit for generating high-voltage pulses for exciting an ultrasonic transducer;
        an adjustable linear gain ultrasonic signal amplification circuit for ultrasonic transducer return signal acquisition; and
        transducer positional control logic circuitry, said control logic circuitry having a plurality of ultrasonic beam configuration settings that are selectable manually or through operation of said digital processor.

2. A computer controlled nondestructive testing system for performing ultrasonic inspections, as set forth in claim 1, wherein said ultrasonic transducer pulser circuit for generating high-voltage pulses is controllable to provide a pulse train of an adjustable duration.

3. A computer controlled nondestructive testing system for performing ultrasonic inspections, as set forth in claim 1, wherein said ultrasonic transducer pulser circuit for generating high-voltage pulses is controllable to provide a pulse train comprised of pulses of an adjustable predetermined duration.

4. A computer controlled nondestructive testing system for performing ultrasonic inspections, as set forth in claim 1, wherein said ultrasonic transducer pulser circuit for generating high-voltage pulses is controllable to provide a pulse train comprised of pulses at an adjustable predetermined frequency.

5. A computer controlled nondestructive testing system, as set forth in claim 1, wherein said pulser-receiver unit comprises a plurality of functionally independent circuits, including a transducer exciter circuit means for generating a pulse train of adjustable duration and a transducer servo-relay control means for controlling a scanning orientation of a transducer, said servo-relay control means further comprising means for allowing either manual or computer-originated control over ultrasonic beam scanning characteristics.

6. A computer controlled nondestructive testing system, as set forth in claim 5, wherein said ultrasonic transducer excitation circuit includes a DC-to-DC converter for providing a high voltage source and generates a high-voltage, variable duration pulse train.

7. A computer controlled nondestructive testing system as set forth in claim 1, wherein said programmable digital processor comprises conventional personal computer system hardware including keyboard, display and monitor.

8. A computer controlled nondestructive testing system as set forth in claim 1, wherein said programmable digital processor includes an interactive operator-machine system interface.

9. In a programmable digital processor controlled ultrasonic diagnostic test equipment arrangement, an interactive operator-machine interface, comprising:
    a programmable digital processor;
    a display device;
    a keyboard input device;
    wherein a plurality of option selection menus is displayed on said display device, said menus allowing an operator to input operational control parameters or choose from a variety of system operational control selections, and wherein said processor is programmed to provide for display on said display device a plurality of option selection menus including a main menu for selecting from a variety of system programs and sub-menus, at least one of said sub-menus comprising a menu for selecting and configuring ultrasonic testing procedures and inputting specific desired test parameters.

10. In a computer controlled nondestructive testing system for performing ultrasonic inspections, said system having a programmable digital processor for data acquisition and equipment control, a modular ultrasonic transducer excitation and return signal amplification circuit arrangement, comprising:
    a plurality of transducer interface circuit cards, each card containing either a transducer excitation circuit or a return signal amplification circuit; and
    a testing system digital control processor having an interactive operator-machine interface including a display device for providing a plurality of selection menus allowing an operator to choose from a variety of system operational control selections, wherein at least one return signal amplification circuit comprises
        a logarithmic-gain ultrasonic signal amplification circuit having a plurality of selectable gain settings, and wherein said gain settings are selectable by said digital processor via said selection menus and are also selectable manually by operation of a selector switch.

11. A computer controlled nondestructive testing system for performing ultrasonic inspections, as set forth in claim 10, wherein said transducer interface circuit cards are plug-in compatible in accordance with at least one of either ISA, EISA or PCI bus conventions.

12. A computer controlled nondestructive testing system for performing ultrasonic inspections, as set forth in claim 10, wherein said transducer interface circuit cards containing said ultrasonic transducer excitation circuit and said logarithmic-gain ultrasonic signal amplification circuit function separately and independently of one another.

13. A computer controlled nondestructive testing system for performing ultrasonic inspections, as set forth in claim 10, ultrasonic transducer excitation and return signal amplification arrangement further comprises a means for generating a video output signal for displaying received ultrasonic transducer return signals.

14. In a programmable digital processor controlled ultrasonic diagnostic test equipment arrangement for performing ultrasonic testing of solid rotor forgings, an interactive operator-machine interface including a display device and a means for inputting operator selections, comprising:

means for displaying on said display device a main testing system menu presenting a selection of submenus and system operation commands for election by an operator, including at least one menu selection for storing and accessing previously stored rotor descriptions and corresponding scanning motion control information; and means for controlling said ultrasonic diagnostic test equipment to initialize the test equipment and perform an ultrasonic diagnostic test in accordance with elections made by an operator.

15. The interactive operator-machine interface according to claim 14, wherein said plurality of submenus include a testing menu, a plotting menu, and a post processing menu.

16. In a computer controlled ultrasonic diagnostic test equipment arrangement having a menu oriented interactive operator-machine system interface comprising a display device for displaying various selection menus and a means for inputting operator selections, a method for selecting and setting desired ultrasonic testing parameters and operations for controlling diagnostic testing procedures, comprising steps of:

(a) presenting on said display device a display of one or more procedure and parameter selection menus;

(b) initializing the test equipment in accordance with selections or information inputted by an operator in response to menus presented in step (a); and (c) conducting ultrasonic scanning and acquisition of data in accordance with selections or information inputted by an operator in response to said menus.

17. In a programmable digital processor controlled ultrasonic diagnostic test equipment arrangement having an interactive operator-machine interface including a display device and a means for inputting operator selections, a method for performing ultrasonic testing of solid forgings, comprising steps of:

(a) displaying on said display device a main testing system menu presenting a selection of submenus and system operation commands for election by an operator, including at least one menu selection for storing and accessing previously stored rotor descriptions and corresponding scanning motion control information; and (c) controlling said ultrasonic diagnostic test equipment to initialize the test equipment and perform an ultrasonic diagnostic test in accordance with elections made by an operator during a display of menu and submenus.

18. In a programmable digital processor controlled ultrasonic diagnostic equipment arrangement for examining rotor forgings, including a display device and a means for inputting operator selections, a method for providing an interactive operator-machine interface, comprising steps of:

(a) displaying on said display device a main menu for selecting from a variety of system programs and sub-menus, said programs and sub-menus providing prompts for selectively arranging ultrasonic testing procedures, configurations and for inputting specific desired test parameters; and (b) configuring the ultrasonic diagnostic equipment in accordance with selections made by a user when viewing the menus.

19. In a programmable digital processor controlled ultrasonic diagnostic equipment arrangement for examining a cylindrical forging, a method of acquiring ultrasonic data indication sets, comprising the steps of:

rotating said forging along its longitudinal axis;

setting up a "zero degree" reference indication with respect to a predetermined rotational position of said cylindrical forging, wherein the "zero degree" reference of said cylindrical forging is determined by monitoring signal pulses generated by a switch actuated by a trip device attached to the cylindrical forging;

generating ultrasonic diagnostic signals and acquiring ultrasonic return signal data from one or more transducers in sliding contact with the forging during each revolution of its rotation; and associating ultrasonic return signal data acquired during a rotation of said cylinder with a position along the cylindrical forging by reference to said "zero degree" reference indication and signal pulses generated by said trip device.

20. A method of acquiring ultrasonic data indication sets as set forth in claim 19 wherein an angular position of said cylindrical forging is determined by counting pulse signals generated by a rotational movement encoder device that monitors rotational movements of an idler wheel device that rests against said rotor and is rotated by rotational movement of said rotor.

* * * * *